United States Patent [19]
Holman

[11] Patent Number: 6,040,188
[45] Date of Patent: Mar. 21, 2000

[54] IN VITRO GASTROINTESTINAL MIMETIC PROTOCOL FOR MEASURING BIOAVAILABLE CONTAMINANTS

[75] Inventor: Hoi-Ying N. Holman, Berkeley, Calif.

[73] Assignee: The Regents of the University of California, Oakland, Calif.

[21] Appl. No.: 09/196,618

[22] Filed: Nov. 18, 1998

Related U.S. Application Data

[60] Provisional application No. 60/066,169, Nov. 18, 1997.

[51] Int. Cl.$^7$ .................................................. G01N 33/92
[52] U.S. Cl. ................................ 436/71; 436/71; 436/60; 436/139; 436/140
[58] Field of Search ................................ 436/60, 71, 140, 436/139, 175, 177; 585/1, 11, 16, 833, 800

[56] References Cited

U.S. PATENT DOCUMENTS

| | | |
|---|---|---|
| 4,927,879 | 5/1990 | Pidgeon . |
| 4,931,498 | 6/1990 | Pidgeon ................................. 525/54.1 |
| 5,462,859 | 10/1995 | Hauser ...................................... 435/29 |
| 5,567,592 | 10/1996 | Benet ..................................... 435/7.21 |
| 5,756,357 | 5/1998 | Wright et al. ............................. 436/25 |

OTHER PUBLICATIONS

Davis, et al., "Micromineralogy of Mine Wastes in Relation to Lead Bioavailability, Butte, Montana," Environmental Science & Technology, V. 27, pp. 1415–1425, (1993).

Staggers, et al., "Physical–Chemical Behavior of Dietary & Biliary Lipids during Intestinal Digestion & Absorption," Biochemistry, V. 29, pp. 2028–2040, (1990).

Katori, et al., "Estimation of Agitation Intensity in the GI Tract in Humans & Dogs Based on In Vitro/In Vivo Correlation," Pharmaceutical Research, V. 12, No. 2, pp. 237–243, (1995).

Minekus, et al., "A Multicompartmental Dynamic Computer–Controlled Model Simulating the Stomach & Small Intestine," ATLA, V. 23, p. 197–209, (1995).

O'Neill, et al., "Modulating Effects in Human Diets of Dietary Fibre & Beef, & of Time & Dose on the Reactive Microcapsule Trapping of Benz[a]pyrene & Metabolites in the Rat Gastrointestinal Tract," Carcinogenesis, vol. 11, No. 4, pp. 599–607, (1990).

Ruby, et al., "Estimation of Lead & Arsenic Bioavailability Using a Physiologically Based Extraction Test," Environmental Science & Technology, V. 30, pp. 422–430, (1996).

Turkall, et al., "Soil Adsorption Alters Kinetics & Bioavailability of Benzene in Orally Exposed Male Rats," Archives of Environmental Contamination & Toxicology, V. 17, pp. 159–164, (1988).

Yvon, et al., "In Vitro Simulation of Gastric Digestion of Milk Proteins: Comparison Between In Vitro & Vivo Data," Journal of Agriculture & Food Chemistry, V. 40, pp. 239–244, (1992).

Hernell, et al., "Physical–Chemical Behavior of Dietary and Biliary Lipids During Internal Digestion and Absorption", Biochemistry, V. 29, pp. 2041–2056, (1990).

Ruby, et al., "Development of an In Vitro Screening Test to Evaluate the In Vivo Bioaccessibility of Ingested Mine–Waste Lead", Environmental Science and Technology, V.27, pp. 2870–2871, (1993).

*Primary Examiner*—Jill Warden
*Assistant Examiner*—Huan Tran
*Attorney, Agent, or Firm*—Paul R. Martin; Henry Sartorio; David J. Aston

[57] ABSTRACT

The present invention relates to measurements of contaminants in the soil and other organic or environmental materials, using a biologically relevant chemical analysis that will measure the amount of contaminants in a given sample that may be expected to be absorbed by a human being ingesting the contaminated soil. According to the present invention, environmental samples to be tested are added to a pre-prepared physiological composition of bile salts and lipids. They are thoroughly mixed and then the resulting mixture is separated e.g. by centrifugation. The supernatant is then analyzed for the presence of contaminants and these concentrations are compared to the level of contaminants in the untreated samples. It is important that the bile salts and lipids be thoroughly pre-mixed to form micelles.

5 Claims, No Drawings

IN VITRO GASTROINTESTINAL MIMETIC PROTOCOL FOR MEASURING BIOAVAILABLE CONTAMINANTS

CROSS REFERENCE TO RELATED APPLICATIONS

This application claims priority to provisional patent application Ser. No. 60/066,169 filed Nov. 18, 1997, hereby incorporated by reference.

STATEMENT REGARDING FEDERAL SPONSORSHIP

This invention was made with U.S. Government support under Contract No. DE-AC03-76SF0098 between the U.S. Department of Energy and the University of California for the operation of Lawrence Berkeley National Laboratory (LBNL). The U.S. Government may have certain rights to this invention.

BACKGROUND OF THE INVENTION

1. Field of the Invention

The present invention relates to measurements of contaminants in the soil and other organic or environmental materials, using a biologically relevant chemical analysis that will measure the amount of contaminants in a given sample that may be expected to be absorbed by a human being ingesting the contaminated soil.

2. Description of the Related Art

The clean up of hazardous wastes in the environment has become a scientific and socially significant problem. As more effort is spent on the clean-up of contaminated environmental sites and other areas of pollution, the need to monitor the efficiency and efficacy of these clean-up methods becomes more pressing.

In many instances, the technical ability to detect contaminating compounds exceeds our ability to remove them. For example, in soil that has been contaminated with petroleum products, these products and their breakdown products can be detected to very minute levels using analytical chemical techniques such as mass spectrometry and gas chromatography (GC/MS). It is not currently possible to remove these breakdown products to an undetectable level. Breakdown products known as polycyclic aromatic hydrocarbons (PAH's) are major concerns in petroleum contamination, due to their carcinogenic effect. This effect is mediated by the oral ingestion of materials, such as soil, which contain small amounts of the PAH's. Children are particularly vulnerable to soil ingestion.

PAH's may consist of 2- to 6-ring polycyclic compounds; their composition varies with the type of contaminated soil.

The standard prior art technique for measuring these contaminants in soil is to extract a soils sample with methylene chloride or other organic solvents or use sonication; separate aliphatics and aromatics according to cleanup methods, and subject all fractions to GC/MS analysis under EPA guidelines.

This regulatory-based approach simplifies risk and exposure assessment by assuming that all contaminants in ingested soil are completely absorbed into the blood stream, i.e. are 100% bioavailable.

This simplified assumption has been used conservatively to assure the protection of public health, particularly for those who have been involuntarily exposed to the contaminants. However, especially for sites that were contaminated years ago, the assumption of 100% bioavailability could overestimate the ecological risk and increase remediation expenses substantially with negligible reduction of risk. Field and laboratory studies have demonstrated that the bioavailability of contaminants from soil to microorganisms and small animals can be significantly less than 100%.

There are three known in vitro approaches for estimating the bioavailability of environmental contaminants in the GI tract: (1) the two stage physiologically based extraction procedure; (2) the everted sac technique and (3) brush border membrane vesicles.

The two-stage physiologically-based extraction procedure employs an extraction procedure designed to simulate the stomach and small intestinal stages of digestion and adsorption of metal ions. The method generally uses solutions of specific pH that contain digestive enzymes (e.g. pepsin in the stomach, pancreatic enzymes and bile acids in the small intestine) mixed with test substrates (e.g. food and soil) to reproduce GI tract function and chemistry. Depending on the GI emptying conditions, a value of pH 1.35–2.0 is selected for the gastric incubations, and pH 7.0–7.5 is selected for the small intestinal incubations. This in vitro method may be simplified by assuming that enzymes have minor influence on the release of metals from soil matrix. At the end of the incubation period, the sample is removed from the incubation flasks, centrifuged, and the supernatant is analyzed. Recently, a continuous flow in vitro method to estimate the bioavailability of zinc and calcium from foods was developed. This method employs a simulated gastric digestion with pepsin, gradual pH change during the first 30 minutes of dialysis in an Amicon stirred cell, and a further two hour of continuous dialysis accompanied by intestinal digestion with pancreatin-bile extract. The percentage of continuously dialyzed metal ions was used to express the bioavailability.

The second approach is based on an everted sac that is prepared by cutting a small segment of the intestine from laboratory animals, everting the segment, filling the sac with 0.5 to 1.0 ml of oxygenated physiological buffer solution, tying off both ends of the sac and incubating it in a well-oxygenated buffer solution containing the test substrates at 37° C. for 15 to 60 minutes. When necessary, the incubating buffer solution would also contain a nonpermeable marker to correct for the volume adherent to the mucosa. The everted sac technique has been used to study the gastrointestinal absorption of inorganic mercuric compounds, aromatic hydrocarbons, and the transport of copper.

The third method involves the isolation of brush border membrane vesicles from intestinal cells. Unlike the everted gut sac technique, this method involves the disruption of the cellular structure followed by either density gradient centrifugation, free-flow electrophoresis, immunoabsorbent chromatography, or precipitation of nonbrush-border membranes through the addition of $Ca^{++}$ or $Mg^{++}$. These isolated membrane vesicles have transport properties similar to in vivo conditions. During the bioavailability experiment, membrane vesicles are incubated in buffer containing the test substrate. At the end of the incubation duration, membrane vesicles are filtered, washed thoroughly, and analyzed for the amount of chemicals being retained. This method has been used for in vitro measurement of absorption of inorganic mercury, the transport and absorption of zinc and the uptake of iron in the intestine. The three categories of in vitro methods described above are mostly designed for single application, include a limited number of simulated parameters, and are not directly applicable for simulating the bioavailability of petroleum, (i.e., hydrophobic) hydrocarbons in human GI tract. The first category is designed mainly for measuring the bioavailability of metals whose solubility is mainly controlled by the pH and mixing intensity. The other two categories are mainly for measuring only the transport and adsorption of chemicals through the intestinal membranes.

When measuring bioavailability of complex mixtures of contaminants, it is important to remember that the human GI tract consists of different anatomical regions with very different biophysico-chemical conditions. For example, petroleum products are a mixture of different classes of organic compounds, and each class may behave differently in different anatomical regions of the human GI tract, thereby influencing the absorption, metabolism, and the ultimate bioavailability to humans. Under these dynamic conditions a more versatile in vitro approach is required. Relevant in this regard are in vitro GI models based on techniques developed for nutritional, pharmacology, and pharmacokinetics use.

Known in vitro pharmacological GI models include (1) the computerized gastro-intestinal model (2) the simulated human intestinal microbial ecosystem (SHIME) (3) the "artificial stomach" and improved dialysis cell (IDC) by Saroie and Gauthier, (1968), J. Food Science 51(2): 494–498. The first category is designed for measuring the bioavailability of metals whose solubility is mainly controlled by the pH and mixing intensity. The other two methods are for measuring only the transport and adsoprtion of chemicals through the intestinal membranes.

In the first model, a multi-compartmental computer-controlled in vitro model was designed to simulate the transit time and dynamic physiological processes occurring within the lumen of the gastrointestinal tract of man and monogastric animals. The computer model implements measurements from in vitro studies to prescribe the biophysico-chemical conditions, and uses exponential equations to control the transit time of chyme in the GI tract. The ability of the model for reproducing in vitro data on meal transit, pH, bile salt concentrations and the absorption of glucose was tested.

SHIME is a 5-step multi-chamber reactor designed mainly to simulate the gastro-intestinal microbial ecosystem in human see (Minekos, et al., A.T.L.A. 23:197–209 (1995)). The small intestine is simulated by a two-step "fill and draw system", and the large intestine by a three-step reactor. The medium used in the reactor system is similar to that of the human gastro-intestinal tract. SHIME has been tested by monitoring fermentation fluxes and products. Measurements show that resulting patterns of microbial diversity and activity are similar to those observed from in vitro studies.

The artificial stomach is an in vitro model which stimulates the digestion of milk protein. It involves the use of a reaction vessel inside a shaken water bath. Computer-controlled peristaltic pumps continuously provided, at a variable rate, additional enzymes and HCl to the reactor, and allowed the collection of digested products. The in vitro results showed good relations with in vitro data.

The artificial stomach model may also be constructed to simulate the gastric secretion and emptying in physiological situations specifically for antacid evaluation. It involves the use of a 'gastric' reservoir and a peristaltic pump to imitate the interaction between secretory flux and variation in emptying fluxes, the presence of proteins, and the human gastric juice of different pH. Measurements obtained from this model show good agreement with clinical data.

IDC is a dialysis cell devised to study in vitro digestion of proteins. It is a modification of a dialysis cell. The cell consists of an inner reaction vessel fixed into a cylindrical outer compartment where buffer circulation is provided. The vessel is surrounded by a tubular membrane with molecular weight cutoff of 1000. The dimensions of the compartment, the membrane, and the buffer flow rate are determined with labeled amino acids prior to the experiment. For the digestion assay, casein is first hydrolyzed with pepsin at pH 1.9 for 30 minutes. The mixture is then made alkaline (pH 7.5) and poured into the dialysis tube with pancreatin. Nitrogenous material collected with the sodium phosphate buffer will be analyzed directly.

Review of the literature on in vitro approaches for determining bioavailability of contaminants in the human GI tract shows that the two-stage physiologically-based method, the everted sac technique, and the brush border membrane vesicles technique are mostly designed for a single application. They generally include a limited number of simulated parameters, and are not directly applicable for simulating the bioavailability of petroleum (hydrophobic) hydrocarbons in human GI tract. At the same time, review of the literature on in vitro methods from areas of nutrition and pharmacology/pharmacokinetics shows that there are a number of models that will provide a set of tools of varying sophistication. However, because some of these models are designed to be used in medical research, they are too expensive and not practical to be used for testing environmental contamination

SUMMARY OF THE INVENTION

According to the present invention, environmental samples to be tested (e.g. soil or water) are added to a pre-prepared physiological composition of bile salts and lipids designed to mimic the effects of the GI tract. They are thoroughly mixed, and graded and then the resulting mixture is separated e.g. by soft centrifugation or filtration. The supernatant is then filtered and analyzed for the presence of contaminants and these concentrations are compared to the level of contaminants in the untreated samples. Contaminants that are readily detectable in untreated samples may be present in vastly lower or undetectable amounts after the present gastrointestinal mimetic protocol has been applied to the sample. This permits an informed decision to be made as to the safety of a given sample in terms of human ingestion of the contaminants. The contaminants may be PAH's, MTBE, chlorinated phenols, or any hydrophobic hydrocarbon.

The present invention comprises a gastrointestinal mixture of compounds representing a simulated intestinal bile salt mixture, namely various cholates and fatty acid salts. The gastrointestinal mixture is chosen on the basis of its ability to mimic conditions in the gut, especially the small intestine. The lipids comprise lecithin (phosphatidyl choline, a phospholipid with a polar head group) and oleic acid and its derivatives. Oleic acid has the formula n-C8H17—C=C—(CH2)7COOH, and its derivatives will have a similar structure of an 18 carbon chain with one double bond, with various substituents.

The present invention further comprises an optional second treatment mimicking the effect of the epithelial cell: an HPLC step. The contaminants are further separated from the soil sample in a mobile phase using an immobile artificial column.

The contaminants are detected in very low levels through the use of a GC/SIM (SIM=selected ion monitoring mass spectrometry), which is more sensitive than conventional GC/MS. Any suitable detection instrument may be used, however.

An important aspect of the present invention is the recognition that the intestine, rather than the mouth or stomach, plays the principal role in organic contaminant uptake. The mouth and stomach serve only to reduce the soil to millimeter-sized particles (i.e. changing the textures of the environmental samples), an effect taken into account in the present protocol. It is also important to recognize that the contaminants must pass through the microvilli of the gastrointestinal system; a 0.1 to 1 micron filter is provided after separation of the supernatant in the present protocol for the purpose of mimicking that portion of the gastrointestinal physiology.

DESCRIPTION OF THE PREFERRED EMBODIMENT

In the preferred embodiment, a composition representing an intestinal bile salt mixture is prepared, comprising at least cholate derivatives, such as glycocholate, glycodeoxycholate, glycochenodeoxcholate; glycolithocholate sulfate and sodium chloride; taurocholate; taurochenodeoxycholate, and taurolithocholate sulfate. Similarly, a simulated mixture of intestinal lipids (M.I.L.) made of oleic acid, monoolein, diolein and lecithin is also supplied. Certain optimal intestinal components, such as cholesterol, and other digestive enzymes are not included in the mixture because they do not play an important role in influencing the uptake of hydrophobic nonpolar organic environmental contaminants that have a xenobiological structure.

This mixture is thoroughly pre-mixed for 24–48 hrs at physiological temperatures so as to achieve micelles of fat within the salt solution. The presence of micelles may be verified by visual observation of fatty globules in the mixture.

The sample is then mechanically reduced to a diameter of 0.1 to 10 millimeters by filtration and/or grinding and added to the mixture. It is stirred in the mixture at an approximate physiological temperature (27–47° C.) and a pH of 6.5–7.3 for 4 to 24 hrs. While not wishing to be bound by any theory of operation for the present method, it is believed by the inventor that ingested residual environmental matrix-bound non-polar hydrophobic hydrocarbons are solubilized by the bile salt micelles present in the upper segment of the small intestine, prior to absorption across the intestinal mucosa. Aqueous solutions of bile salt in the intestine exhibit an abrupt change in their physical properties over a narrow concentration range. This change is due to the formation of oriented aggregates or micelles. The narrow bile salt concentration range at which micelles begin to form is referred to as the critical concentration for micelle formation (CMC). Micellar solubilization of a poorly soluble soil-bound contaminant occurs in the small intestine, rather than other parts of the GI tract, through interaction of the contaminants with these micelles. An effective, reproducible and accurate in vitro method of modeling the oral availability of contaminants can be achieved by mimicking micellar conditions in the small intestine.

The preferred embodiment is directed to environmental matrix contaminated with crude and refinery products, asphalt-type material, heavy sealant, diesel, gasoline, jet fuel and the like. The invention, in view of the description below, may be readily adapted to food, water, biota and other sample types, and other hydrophobic, non-polar organic contaminants.

Materials

Soil samples were used as received. Reagent grade (Sigma) anhydrous sodium phosphate and sodium biphosphate were used as received. Reagent grade sodium chlorides were roasted at 600° C. for four hours to oxidize and remove any organic impurity. Ten pure conjugated bile salts, which represent those found in the human intestinal bile content, were purchased from Cal Biochem-Beh and Sigma, namely sodium glycocholate, sodium glycochenodeoxycholate, sodium glycodeoxycholate, sodium glycolithocholate, disodium glycolithocholate sulfate, sodium taurocholate, sodium taurochenodeoxycholate, sodium taurodeoxycholate, sodium taurolithocholate, disodium taurolithocholate sulfate. They were dried in vacuo for 36 hours prior to use. They were used as a mixture to examine their influence on solubilization of ingested soil-bound PAH's, alone and in the presence of intestinal lipids. The lipid components were those which are normally found as components of either the human bile or the end products resulting from enzymatic action of pancreatic lipase during the process of digestion of ingested dietary triglycerides. The former components are represented by cholesterol and lecithin, the latter by lauric acid, myristic acid, palmitic acid, 1-monolaurin, 1-monoyristin and 1-monostearin.

All glassware used was autoclaved. All solutions were prepared at 4° C. with deionized and organic-free water that had been filtered through a $0.2\mu$ filter in the presence of ultraviolet light shortly prior to the experiment. They were kept at 4° C. when not in use. Solutions prepared and sterilized in this manner showed no evidence of bacterial growth during the experimental time.

A Simulated Human Intestinal Bile Salt Mixture

A stock bile salt solution was prepared containing 0.024M sodium glycocholate, 0.024M sodium glycochenodeoxcholate, 0.016M sodium glycodeoxycholate, 0.0007M sodium glycolithocholate, 0.003M disodium glycolithocholate sulfate, 0.012 sodium taurocholate, 0.012M sodium taurochenodeoxycholate, 0.008M sodium taurodeoxycholate, 0.0003M sodium taurolithocholate, 0.001M disodium taurolithocholate sulfate, and 0.05 sodium chloride. The final solution was thus 0.1M with respect to the total bile salt concentration, and 0.15M with respect to sodium ion concentration.

A pH 7.3 phosphate buffer stock solution was prepared shortly before the experiment for use in a pH 6.8 solution. A 0.3M monobasic sodium phosphate $NaH_2PO_4$ and a 0.15M dibasic sodium phosphate $Na_2HPO_4$ solution were mixed in a ratio of 55 parts of the former solution to 45 parts of the latter solution. The resulting solution was thus 0.3M with respect to sodium ion concentration. This stock solution was diluted 1:1 (v:v) with filter-sterile deionized distilled water under ultraviolet light immediately before use (as working solution).

The concentration of the simulated intestinal bile salt mixture was varied from 0–0.06M by volumetrically mixing the 0.1M stock solution with appropriate volume of pH 6.8 buffer working solution. The preparation was conducted under ultraviolet light. The pH of a 0.06M bile solution prepared in this manner was approximately 6.5 at 37° C. The sodium ion concentration remained to be 0.15M.

Simulated Intestinal Lipid Additives

Lipid solutions were prepared to have a total lipid concentration of 1–1.5 g/100 mL. 1–1.5 mole % represents the lipids; or when MBS:MIL is 100:00 or 90:10, cholesterol's maximum solubility is about 2 mole %.

| Composition | Species | Mole Ratio | Mole % | Mol. Wt | g/100 ml Solution |
|---|---|---|---|---|---|
| A | Oleic Acid | 5 | 69.4 | 283 | 0.698 |
|  | Monoolein | 1 | 13.9 | 357 | 0.139 |
|  | Diolein | 0.2 | 2.8 | 621 | 0.28 |
|  | Lecithin | 1 | 13.9 | 787 | 0.139 |
|  |  | Total: | 100.0 | Ave.: 372.8 | 0.027M |
| B | Oleic Acid | 10 | 82.0 | 283 | 0.820 |
|  | Monoolein | 1 | 8.2 | 357 | 0.082 |
|  | Diolein | 0.22 | 1.6 | 621 | 0.016 |
|  | Lecithin | 1 | 8.2 | 787 | 0.082 |
|  |  | Total: | 100.0 | Ave.: 335.8 | 0.030M |
| C | Oleic Acid | 20 | 90.0 | 283 | 0.900 |
|  | Monoolein | 1 | 4.5 | 357 | 0.045 |
|  | Diolein | 0.2 | 0.9 | 621 | 0.009 |
|  | Lecithin | 1 | 4.5 | 787 | 0.045 |
|  |  | Total: | 100.0 | Ave.: 312.1 | 0.0302M |

All of the above compositions form mixed micelles with the conjugated bile salts in the small intestine. The particular solution to be used will depend on the solubilization of the water insoluble contaminant under study.

The solubility (mole of chemical/100 ml solution) of a chemical will increase with bile salt concentration (mole of bile salt/100 ml solution), after the bile salt concentration has exceeded the CMC.

EXAMPLE 1

A synthetic human intestinal bile salt mixture, synthetic intestinal lipid mixtures, a phosphate buffer solution and degassed, sterilized, particle-free, deionized and organic free water were prepared according to the procedures described above.

Into the concentrated bile salt stock solution were dissolved the four individual lipids described above. This was done at 4° C. under sterile conditions, each addition taking about one hour. The pH 6.5 phosphate buffer was then added in sufficient quantity to obtain the desired bile salt and lipid concentrations. It is important that the pH of the working mixture be approximately 6.5–7.3.

A 250 mL gas-tight flask was then filled with this solution. It was incubated at 37° C. for 48 hours under constant stirring at 20 rpm using a floating stirrer. It is highly preferred to use a floating stirring ball rather than another mechanical mixing device. It is also highly preferred to use a slow mixing speed of 20–50 rpm, and to use a mixing time of 24–48 hrs.

0.4–0.5 g of well sorted soil (ground to 1 mm particle size) was then added, and the mixture was stirred for an additional 4 hrs under the previous conditions (37° C. at 20 rpm).

After mixing of the ground soil sample and the working solution, the mixture was centrifuged under gentle conditions, sufficient only to separate the supernatant from the soil particles. The supernatant was then passed through a 0.45 micron hydrophobic syringe filter. The concentration of the target compounds was then measured in the supernatant using a conventional CG-SIM (Gas chromatograph, secondary ion, or selected ion monitoring mass spectrometer).

The foregoing protocol was applied to seven soil samples designated A, B, C, E, F, I, J and M.

Table 1 below shows the percent by weight composition of these soil samples:

TABLE 1

|  | SILT | SAND | CLAY |
|---|---|---|---|
| A | 70 | 20 | 30 |
| B | 80 | 45 | 20 |
| C | 45 | 30 | 55 |
| D | 95 | 50 | 5 |
| E | 92 | 68 | 8 |
| F | 12 | 70 | 88 |
| I | 88 | 70 | 12 |
| J | 85 | 55 | 15 |
| K | 80 | 60 | 20 |
| M | 98 | 90 | 2 |

These soil samples were analyzed for polyaromatic hydrocarbon content. Table 2 below shows the PAH concentrations ($\mu$g/kg) as measured directly in the soil by GC/SIM:

TABLE 2

PAH-Soil
PAH Concentrations by Ring ($\mu$g/kg)

|  | A | B | C | D | E | F | I | J | K | M |
|---|---|---|---|---|---|---|---|---|---|---|
| 2-Ring | 5350 | 1100 | 100 | 0 | 8750 | 72 | 2508 | 0 | 0 | 0 |
| 3-Ring | 3878 | 3090 | 0 | 0 | 908 | 404 | 1850 | 0 | 0 | 0 |
| 4-Ring | 429 | 27500 | 840 | 0 | 67 | 1895 | 86 | 3000 | 0 | 135 |
| 5-Ring | 0 | 14150 | 315 | 0 | 0 | 730 | 0 | 0 | 0 | 21 |
| 6-Ring | 0 | 5100 | 275 | 0 | 0 | 120 | 0 | 0 | 0 | 0 |

Table 3 below shows the results in the eight soil samples tested after the present gastromimetic protocol was carried out:

TABLE 3

| | LIPID DIGESTION | | | | |
|---|---|---|---|---|---|
| Soil | 2-ring | 3-ring | 4-ring | 5-ring | 6-ring |
| A | U | [53] | U | — | — |
|  |  | [40] |  |  |  |
| B | U | U | [13] | [17] | [38] |
|  |  |  | [9] | [7] | [13] |
| C | U | — | [52] | U | U |
| E | U | U | U | — | — |
| F | U | U | U | U | U |
| I | U | U | U | — | — |

TABLE 3-continued

| | | | LIPID DIGESTION | | |
|---|---|---|---|---|---|
| Soil | 2-ring | 3-ring | 4-ring | 5-ring | 6-ring |
| J | — | — | [7] [5] | — | — |
| M | — | — | U | U | — |

In the above Table 3, U means below the detection limit of the GC/SIM instrument used. The numbers expressed in brackets represent the amounts of compounds detected as a percentage of the compounds that were detected. The numbers expressed in parentheses represent the amounts of compounds detected after the HPLC step. The bracketed number therefore corresponds to the percentage of target PAH's that can potentially enter epithelial cells of the gastrointestinal tract; and the number in parentheses represents the percent of the ingested target PAH's that can diffuse across the epithelial cells and enter the blood stream. The designated "U" means below the detection limit. The designation "—" means not detected in the original soil sample.

The GC/SIM analysis was carried out by Sequoia Analytical. The detection range was set for 80–650 daltons. If other types of organic contaminants were to be detected, the detection limits would be adjusted accordingly.

The actual compounds detected in a representative soil sample are set forth below in Table 4:

TABLE 4

| | Compounds | Quant Sig Mass | Final (µg/L) |
|---|---|---|---|
| 1 | 1,4-Dichlorobenzene-d4 | | |
| 2 | Nitrobenzene-d5 (S) | 152 | 3516 |
| 3 | Naphthalene-d8 (IS) | 82 | |
| 4 | Naphthalene | 136 | |
| 7 | 2-Fluorobiphenyl (S) | 128 | 5,406(a) |
| 9 | Acenaphthene-d10 (IS) | 172 | 4117 |
| 10 | Acenaphthene | 164 | |
| 11 | Fluorene | 154 | 1.447(aM) |
| 12 | Phenanthrene-d10 (IS) | 166 | 0.2641(aQM) |
| 14 | Anthracene | 188 | |
| 15 | Fluoranthene | 202 | 0.6341(aM) |
| 16 | Pyrene | 202 | 0.1280(aM) |
| 17 | Terphenyl-d14 (S) | 244 | 0.1076(aM) |
| 18 | Benzo (a) anthracene | 228 | 2612 |
| 19 | Chrysene-d12 (IS) | 240 | 1.371(a) |
| 24 | Perylene-d12 (IS) | 264 | |

The legend a means below limit of quantitation, Q means qualifier signal failed the ratio test; M means that the compound response was manually integrated; IS means internal standard and S means standard.

EXAMPLE 2

As an optional second step, the samples processed in accordance with Example 1 may be further processed in a gastromimetic protocol that mimics the effect of the gastrointestinal epithelial cells insofar as these cells further limit the amount of a contaminant that enters the circulation. These cells are shed every 36 hours and also contain biological mechanisms for the degradation and expulsion of contaminants.

The samples obtained from Example 1 were placed on an HPLC column and treated as described in U.S. Pat. No. 4,927,879 and U.S. Pat. No. 4,931,498, the disclosures of which are hereby incorporated by reference.

The HPLC material was selected on the basis of its correlation to epithelial cells. The preferred materials for use in the immobilized membrane structure are phospholipids. The preferred column is manufactured by Regis Technologies, Inc., Morton Grove, Ill.

Alternative Embodiments

The preferred samples for testing are soils. However, water foods and other potentially ingestible materials may be tested. The contaminants to be detected in the present gastromimetic protocol are preferably petroleum breakdown products, e.g. polycyclic aromatic compounds; however, other hydrophobic, lipophilic hydrocarbon compounds may be assayed according to the present protocol, such as pesticides, chlorinated phenols produced by wood processing, other petroleum additives (e.g. MTBE, or methyl tert-butyl ether), etc.

Having described the preferred embodiment of the present invention in sufficient detail to enable the making and using of same, the subject matter to which the inventors claim an exclusive right is set forth below in the appended claims.

What is claimed is:

1. A method for measuring hydrocarbon contaminants in an environmental sample comprising the steps of:

a) processing said sample to exclude particles over 1–10 mm in diameter;

b) preparing a mixture of lipids and bile salts so as to form micelles; then c) adding said processed sample to the mixture to form a sample-lipid-bile salt mixture composition;

d) holding the sample-lipid-bile salt mixture composition at a temperature between 20 and 40° C. for 2 to 12 hrs wherein the sample-lipid-bile salt mixture composition separates into a liquid phase and a solid phase; then e) separating the liquid phase from said solid phase of said sample-lipid-bile salt mixture composition; and f) measuring the amount of said hydrocarbon contaminants in said liquid phase, whereby the measurement of said hydrocarbon contaminants in said liquid phase represents a fraction of said hydrocarbon contaminants in the environmental sample which would be taken up through oral ingestion of the environmental sample.

2. The method of claim 1 wherein said environmental sample is soil.

3. The method of claim 1 wherein said hydrocarbon contaminants are polyaromatic hydrocarbons.

4. The method of claim 1 wherein said mixture of lipids and bile salts consists essentially of salts of glycocholate, glycochenodeoxycholate, glycodeoxycholate; glycolithocholate sulfate; taurocholate; taurochenodeoxycholate; taurolithocholate; glycochenodeoxycholate; glycolithocholate; taurodeoxycholate; and taurolithocholate sulfate thoroughly suspended in a suitable buffer.

5. The method of claim 1 further comprising the step of applying said liquid phase to an HPLC column after step (e).

* * * * *